(12) United States Patent
Chappelow et al.

(10) Patent No.: US 9,774,838 B2
(45) Date of Patent: Sep. 26, 2017

(54) AMBIENT LIGHT SUPPRESSION USING COLOR SPACE INFORMATION TO DERIVE PIXEL-WISE ATTENUATION FACTORS

(71) Applicant: ACCURAY INCORPORATED, Sunnyvale, CA (US)

(72) Inventors: Jonathan Chappelow, Campbell, CA (US); Petr Jordan, Redwood City, CA (US); Jian Gao, San Jose, CA (US); Sarbjit Singh, San Jose, CA (US); Trevor Laing, San Jose, CA (US); Calvin Maurer, San Jose, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 0 days.

(21) Appl. No.: 14/973,406

(22) Filed: Dec. 17, 2015

(65) Prior Publication Data

US 2016/0366385 A1 Dec. 15, 2016

Related U.S. Application Data

(60) Provisional application No. 62/175,149, filed on Jun. 12, 2015.

(51) Int. Cl.
| | |
|---|---|
| *G06K 9/00* | (2006.01) |
| *H04N 9/64* | (2006.01) |
| *A61N 5/10* | (2006.01) |
| *H04N 5/225* | (2006.01) |
| *H04N 9/73* | (2006.01) |

(Continued)

(52) U.S. Cl.
CPC ............. *H04N 9/646* (2013.01); *A61B 6/50* (2013.01); *A61N 5/1045* (2013.01); *G06T 7/13* (2017.01); *G06T 7/70* (2017.01); *G06T 7/90* (2017.01); *G21K 1/046* (2013.01); *H04N 5/2254* (2013.01);

(Continued)

(58) Field of Classification Search
CPC ........... A61N 5/1045; G06T 7/13; G06T 7/70; G06T 7/90; G21K 1/046; H04N 5/2254; H04N 9/646; H04N 9/735
See application file for complete search history.

(56) References Cited

U.S. PATENT DOCUMENTS 4,672,212 A * 6/1987 Brahme ................... G21K 1/02
 250/505.1
4,882,741 A * 11/1989 Brown ................. A61N 5/1042
 378/152

(Continued)

OTHER PUBLICATIONS

International Search Report and Written Opinion dated Jul. 1, 2016, for PCT/US2016/023450, 11 pages.

*Primary Examiner* — Amara Abdi
(74) *Attorney, Agent, or Firm* — Womble Carlyle Sandridge & Rice LLP

(57) ABSTRACT

A method of ambient light suppression in an imaging system, including illuminating leaves of a multi-leaf collimator (MLC) with a first light of a lighting system inside a housing of the MCL, receiving ambient light inside the housing of the MLC through an aperture of the MLC, and capturing, using an imaging system having optics situated inside the housing of the MLC, an image of the leaves of the MLC illuminated with the first light and the ambient light. The method may further include, suppressing the ambient light in the first image to generate a second image of the leaves of the MLC and detecting a feature of the leaves of the MLC in the second image.

24 Claims, 11 Drawing Sheets

(51) Int. Cl.
  *G21K 1/04* (2006.01)
  *G06T 7/70* (2017.01)
  *G06T 7/13* (2017.01)
  *G06T 7/90* (2017.01)
  *A61B 6/00* (2006.01)
  *A61B 6/02* (2006.01)
  *A61B 6/03* (2006.01)

(52) U.S. Cl.
  CPC .............. *H04N 9/735* (2013.01); *A61B 6/022* (2013.01); *A61B 6/032* (2013.01)

(56) References Cited

U.S. PATENT DOCUMENTS

| | | | | |
|---|---|---|---|---|
| 2004/0165065 A1* | 8/2004 | Smith | .................. | H04N 17/002 348/175 |
| 2007/0176126 A1* | 8/2007 | Hashimoto | .......... | A61N 5/1048 250/495.1 |
| 2008/0174673 A1* | 7/2008 | Takahashi | ............... | H04N 9/735 348/223.1 |
| 2012/0141014 A1* | 6/2012 | Lepikhin | ................ | H04N 9/735 382/154 |
| 2012/0201919 A1* | 8/2012 | Pinchot | ................ | A23N 17/005 425/202 |
| 2012/0309636 A1* | 12/2012 | Gibbons | ............... | B01L 3/0275 506/9 |
| 2013/0077844 A1* | 3/2013 | Vija | ...................... | G06T 7/0012 382/131 |
| 2014/0077098 A1* | 3/2014 | Tachikawa | ........... | A61N 5/1045 250/397 |
| 2014/0201670 A1* | 7/2014 | Mallya | .................. | G06F 3/0481 715/771 |
| 2014/0270365 A1* | 9/2014 | Mostafavi | ................ | A61B 6/52 382/103 |

\* cited by examiner

AMBIENT LIGHT SUPPRESSION USING COLOR SPACE INFORMATION TO DERIVE PIXEL-WISE ATTENUATION FACTORS

RELATED APPLICATIONS

This application claims priority to U.S. Provisional Patent App. No. 62/175,149 filed Jun. 12, 2015, which is hereby incorporated by reference in its entirety.

TECHNICAL FIELD

Embodiments of the present disclosure relate to an optical camera based tracking system for a multi-leaf collimator (MLC) used in radiation treatment systems and, in particular, to suppressing effects of ambient light entering the MLC housing on the camera based tracking system.

BACKGROUND

Collimators are frequently used in radiation treatment for shaping a beam of highly energized particles, referred to as a treatment beam. Some radiation treatment systems use a variable aperture collimator called a multi-leaf collimator (MLC). A multi-leaf collimator is a collimator that is made up of a collection of individual leaves that can move independently in and out of the path of the treatment beam. For conformal radiation treatments, the MLC enables conformal shaping of the treatment beam. Accordingly, an image-based feedback can be used to ensure accurate placement of the individual leaves.

BRIEF DESCRIPTION OF THE DRAWINGS

The present disclosure is illustrated by way of example, and not by way of limitation, in the figures of the accompanying drawings.

DETAILED DESCRIPTION

Described herein is a method for suppressing effects of ambient light on a camera based tracking system. In one embodiment, to enable visual tracking and verification of MLC leaf positions in linear accelerator of a radiation treatment system, a camera-based leaf positon feedback system having a camera located inside the collimator housing, is implemented. The camera-based leaf tracking system operates by detecting leaf features (e.g., notch, edge, protrusion, etc.) visible on images of leaf surface. Because the camera is located inside the collimator housing where lighting is minimal, an LED lighting system located inside the housing is used to illuminate the surface of the leaves with light. External light may enter the collimator housing and reflect off the sides of the leaves on the inside of the aperture. This creates undesirable illumination in the aperture, including near the leading edges of the leaves that shape the aperture. Such illumination can make visual tracking and verification of leaf position difficult.

Embodiments of the present disclosure describe ambient light suppressing techniques that may include white balancing operations, determining color saturation, producing an ambient light attenuation map and applying the ambient light attenuation map to the original image. Various embodiments allow for an accurate visual verification of the location of the leaves by reducing undesired illumination throughout the aperture and, in particular, near the leading edges of the leaves that shape the aperture. In addition, these embodiments may be applied to other types of imaging systems that are subject to ambient light effects. In one embodiment, the camera-based feedback system may be a primary feedback system. In another embodiment, the camera-based feedback system may be a secondary feedback system.

Figure 1A:
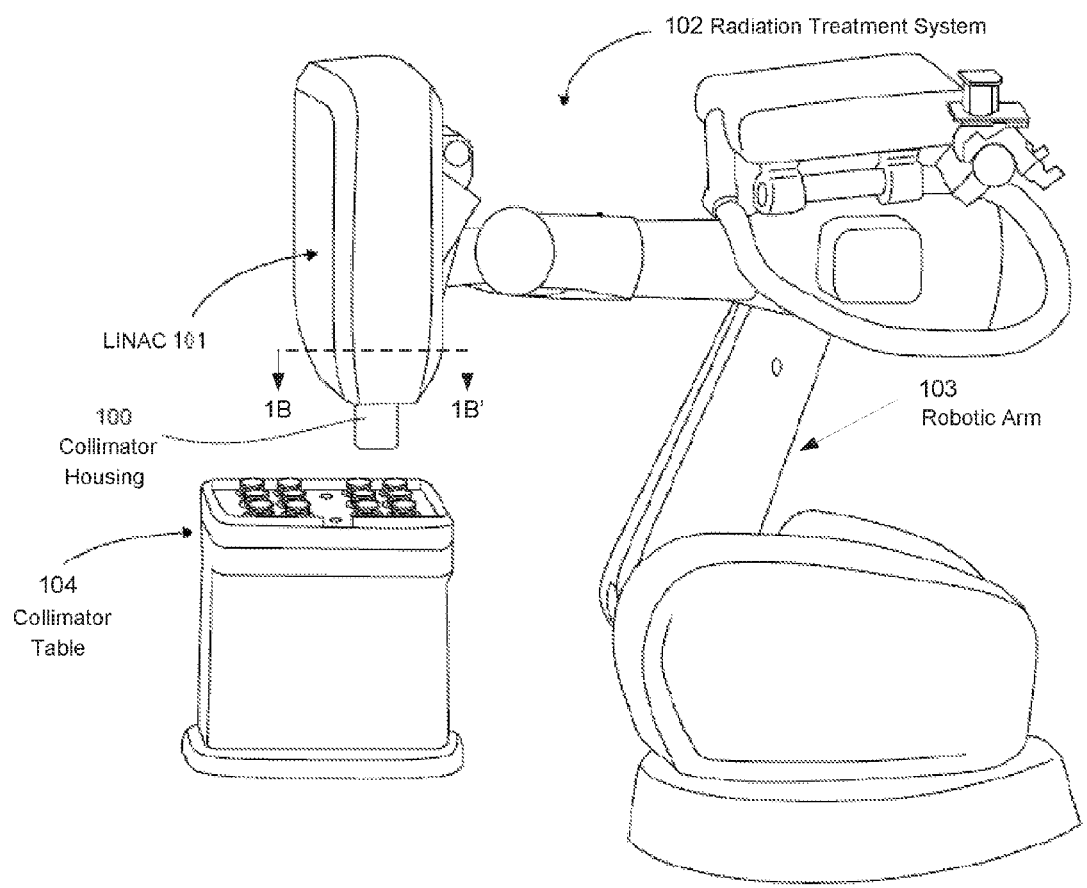
FIG. 1A illustrates one embodiment of a components of a radiation treatment system having a robot based LINAC with a changeable variable aperture collimator, in accordance with embodiments of the present disclosure.

It should be noted that while certain embodiments may be described herein in relation to white light, the method described herein may also be used with any characterized light source (knowing the primary color wavelength). The color may be selected based on the operating environment in order to maximize color separation between the internal system and ambient light. The color selection may be done at the time of installation of the LINAC 101 at a treatment facility or at the time of manufacturing. For example, if a lighting system is also installed in the treatment room, a desired internal color could be selected for the installation. Alternatively, at the time of installation of LINAC 101, a sensor could be held in the MLC aperture (e.g., illustrated by aperture 202) with MLC lighting system 107 turned off to measure the color of the ambient light in the MLC. In this embodiment, any color deemed too close to the measured color (e.g., using a metric such as the Delta-E metric used by the International Commission on Illumination (CIE) to compute the most different color, or an L2 distance in RGB/chromaticity space) would be considered ambient. This may eliminate a need for a white balancing operation (e.g., operation 420 of FIG. 4) discussed below that may be performed in accordance with one embodiment. In one particular embodiment, to maximize system performance, the ambient lighting conditions of a radiation treatment room, in which the MLC housing is used, may be analyzed to determine the most dissimilar MLC lighting color (wavelength) which may be performed in various ways. In one embodiment, if the ambient light is BLUE ([0,0,1]) in RGB space, for example, the optimal internal light may be YELLOW ([1,1,0]) which is a combination of RED and GREEN resulting in the largest separation along the three independent color axes. Another way to quantify the separation is in Hue, Saturation and Value (HSV) space where the first channel is hue/chrome. FIGS. 1A and 1C illustrate different views of embodiments of components of a radiation treatment system having a robot based linear accelerator (LINAC) 101 with a changeable collimator 100. In one embodiment, the radiation treatment system 102 includes a radiation treatment robot having a LINAC 101 mounted on a robotic arm 103. Collimator housing 100 may contain any one of various types of collimators (e.g., an iris collimator, an MLC, etc.) of different apertures that may be detachably mounted to the LINAC 101. The different collimators may reside in collimator table 104, where the radiation treatment robotic may be moved to pick up and drop off collimators based on the collimator type. The particular aperture is matched to the specifics of a radiation treatment plan. In the embodiments described below, collimator housing 100 represents a collimator housing that includes a MLC. In alternative embodiments, the methods described herein may be used with other types of variable aperture collimators and other types of radiation treatment systems (e.g., gantry based LINAC treatment systems).

Figure 1B:
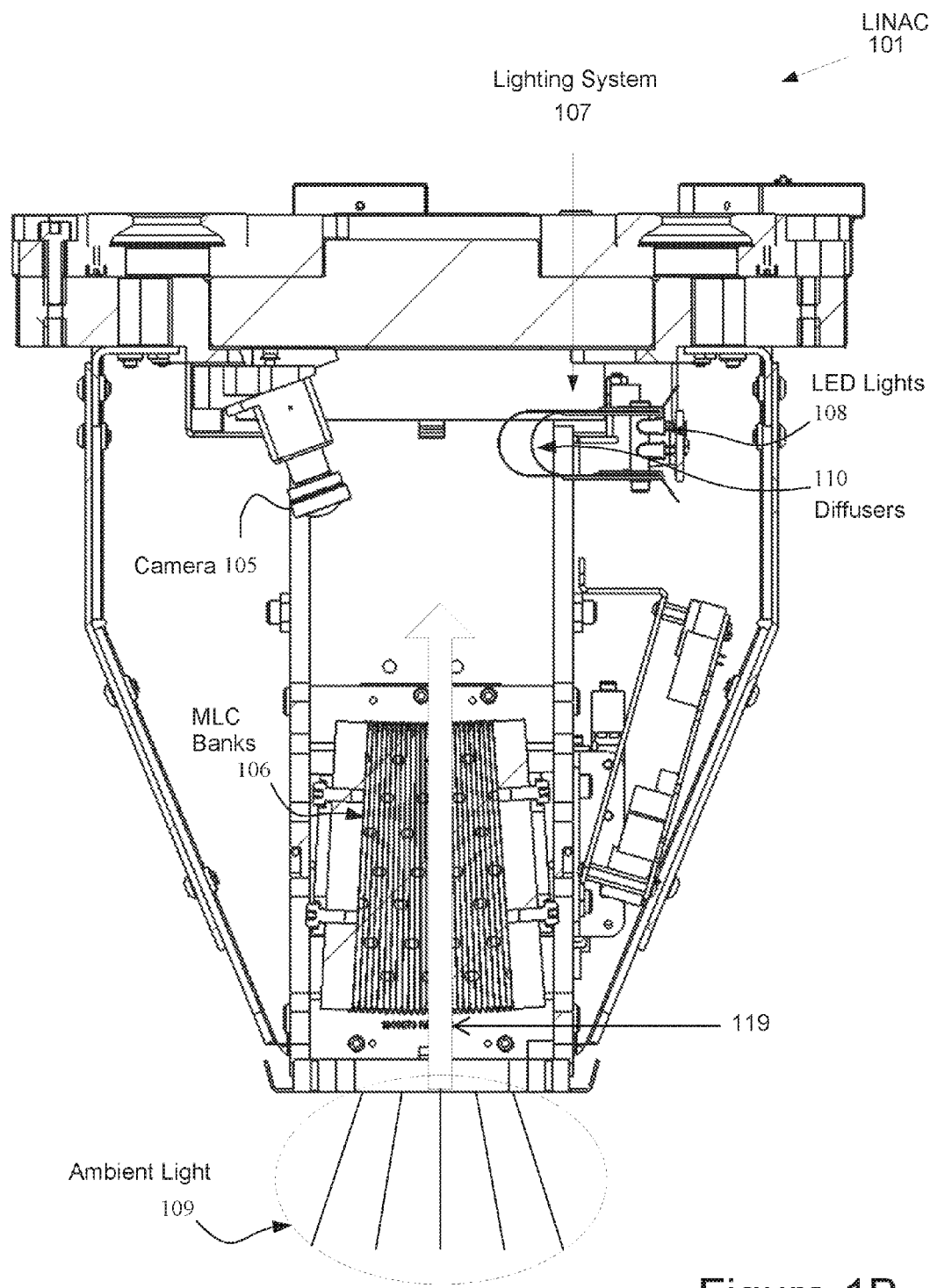
FIG. 1B illustrates a MLC housing utilizing a camera feedback system to verify leaf location, in accordance with embodiments of the present disclosure.
Figure 1C:
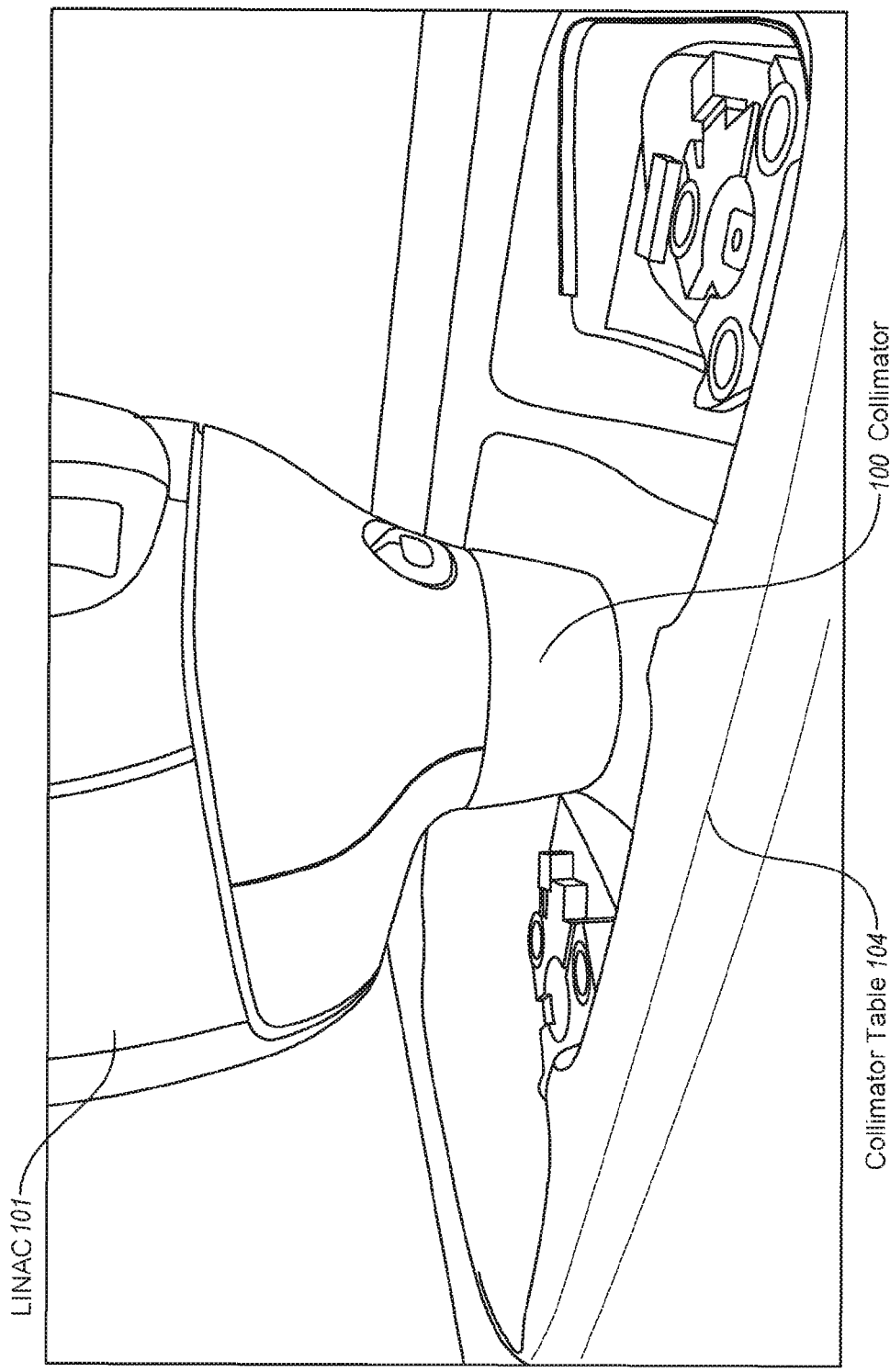
FIG. 1C illustrates another embodiment of components of a radiation treatment system having a robot based LINAC with a changeable variable aperture collimator, in accordance with embodiments of the present disclosure.

FIG. 1B illustrates a cross sectional side view 1B-1B' taken from FIG. 1A of MLC housing 100. MLC housing 100 includes an internal (e.g., LED) lighting system 107, including LED lights 108 and diffusers 110, that is used to illuminate the interior of the MLC housing 100. The camera feedback system utilizes a camera 105 to capture live images of the individual leaf locations of the MLC banks (e.g., 106). It should be noted that camera 105 may include optics and an image sensor including other electronics associated with camera 105, located farther away from the beam path so as not to be effected by the radiation beam. Camera 105, and its associated electronics, and lighting system 107, may be part of the camera feedback system that is connected to the digital processing system 670. Digital processing system 670 is further described in relation to FIG. 6 with respect to the implementation of the operations described in relation to FIG. 4.

Figure 2A:
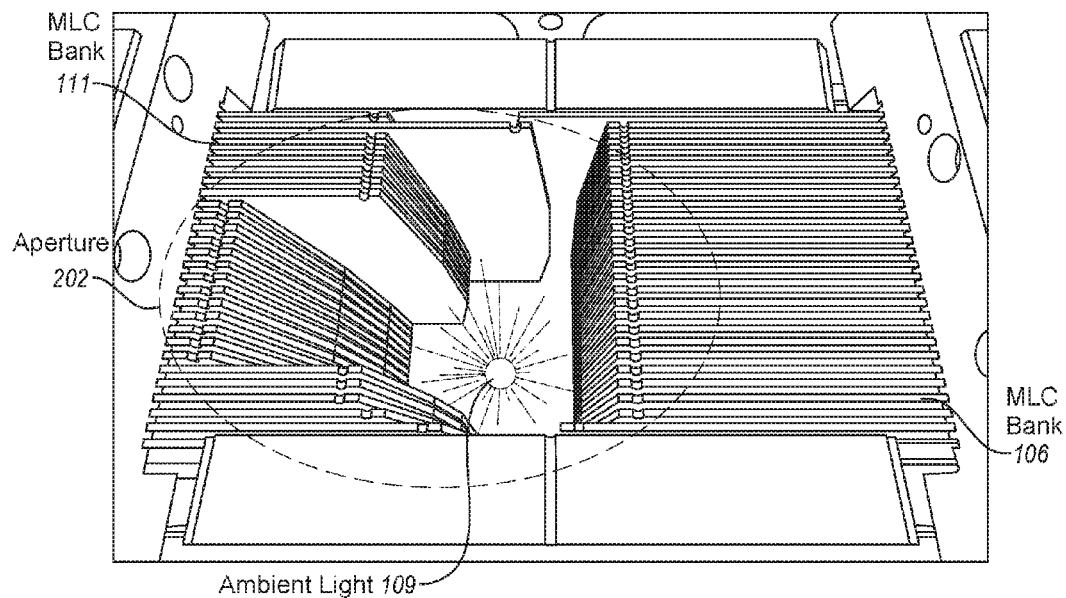
FIGS. 2A-B illustrates views from inside the MLC housing, where ambient light is entering through the aperture of the MLC, in accordance with embodiments of the present disclosure.
Figure 2B:
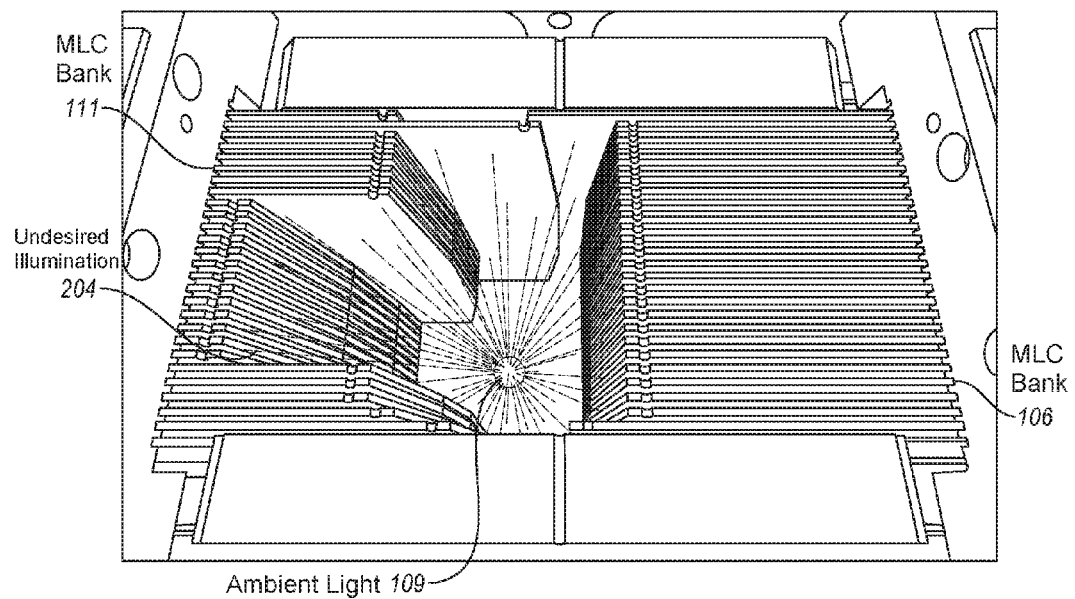

During operation of the LINAC 101, ambient light 109 enters the MLC housing 100 (represented by vector 119) through an aperture between two banks of leaves in the MLC housing 100. It should be noted that since FIG. 1B is a cross section side view of the MLC housing 100, only one of the banks of leaves is shown in the figure. The aperture is an opening between two banks of leaves that allows for the passage of radiation beams generated by the LINAC 101, as illustrated in FIGS. 2A-B. As the ambient light 109 passes through the aperture formed by the MLC bank 106 and opposing bank 111, it reflects off the sides of the leaves on the inside of the aperture.

FIG. 2A illustrates a view from inside the MLC housing 100 as captured by the camera 105 of FIG. 1. As the ambient light 109 enters the MLC housing 100 it reflects off the sides of the leaves of the MLC bank 106 on the inside of the aperture in the general region indicated by the dashed ellipse 202. It should be noted that the aperture may be the region formed by the central, leading edges of the leaves of the MLC banks 106 and 111. FIG. 2B illustrates the undesired illumination 204 near the central, leading edges of the leaves of the MLC banks 106 and 111 caused by the ambient light 109. The undesired illumination 204 (whose shape is more illustrative of the aperture generally identified by reference numeral 202) can affect the ability of the camera feedback system to determine and verify the location of the individual leaves of the MLC banks 106 and 111 by creating visual patterns in the aperture that may falsely be identified as a trackable leaf feature (which, in one embodiment, may be a notch in the leaf but can also be other types of features such as an edge of a leaf) and by changing the appearance of the image near the actual trackable leaf feature.

Figure 3:
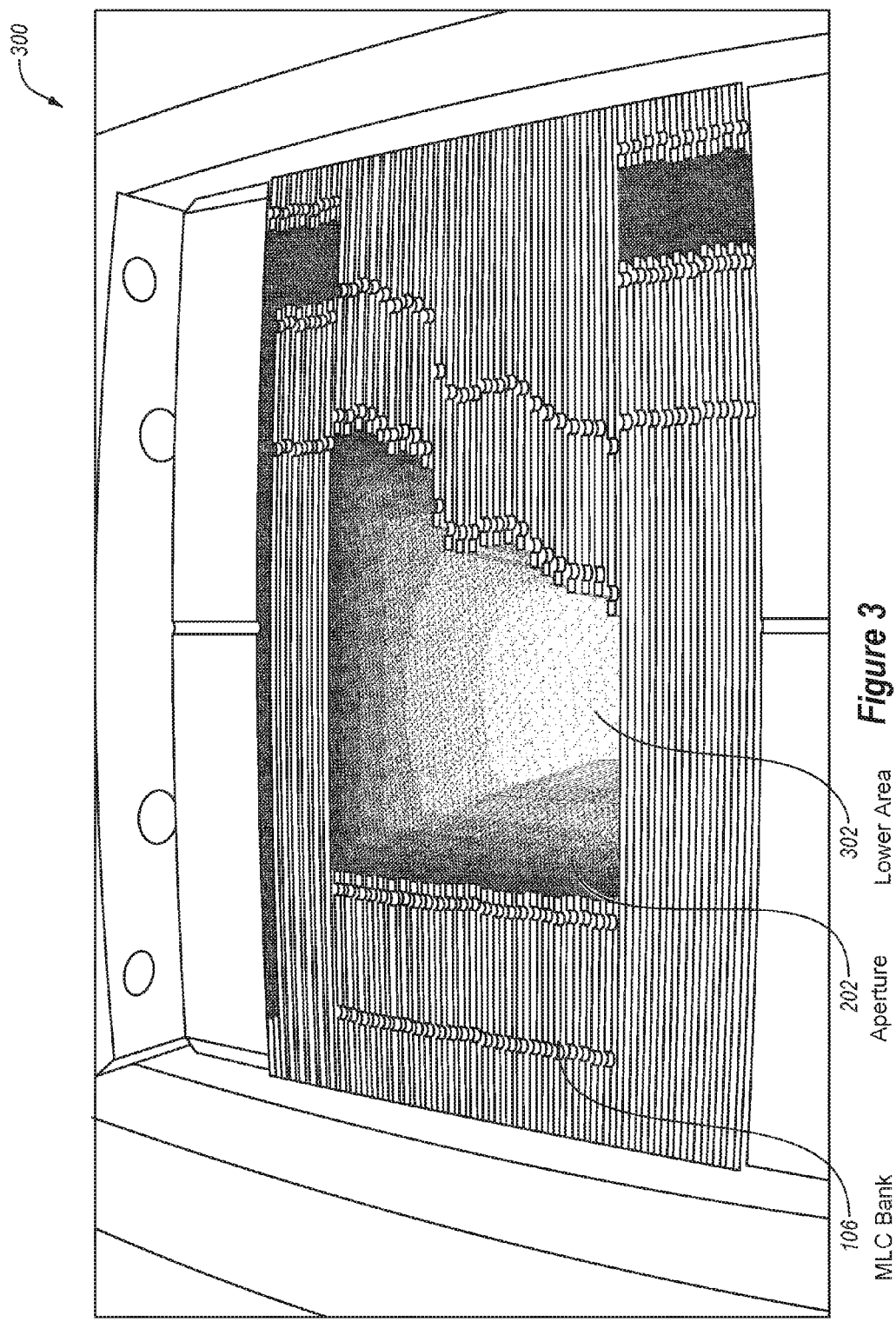
FIG. 3 illustrates a feedback camera image of an MLC aperture, in accordance with embodiments of the present disclosure.

FIG. 3 illustrates an image 300 of the inside surface of the MLC housing 100 from the perspective of the optical imaging system. Ambient light enters through the aperture 202 (whose reference numeral arrow pointing to the central area formed by the leading edges of the leaves of MLC bank 106), illuminating the metallic surfaces located inside the MLC housing 100 of FIG. 1. Here, ambient light is shown as more greatly illuminating the lower area 302 of aperture 202.

Figure 4:
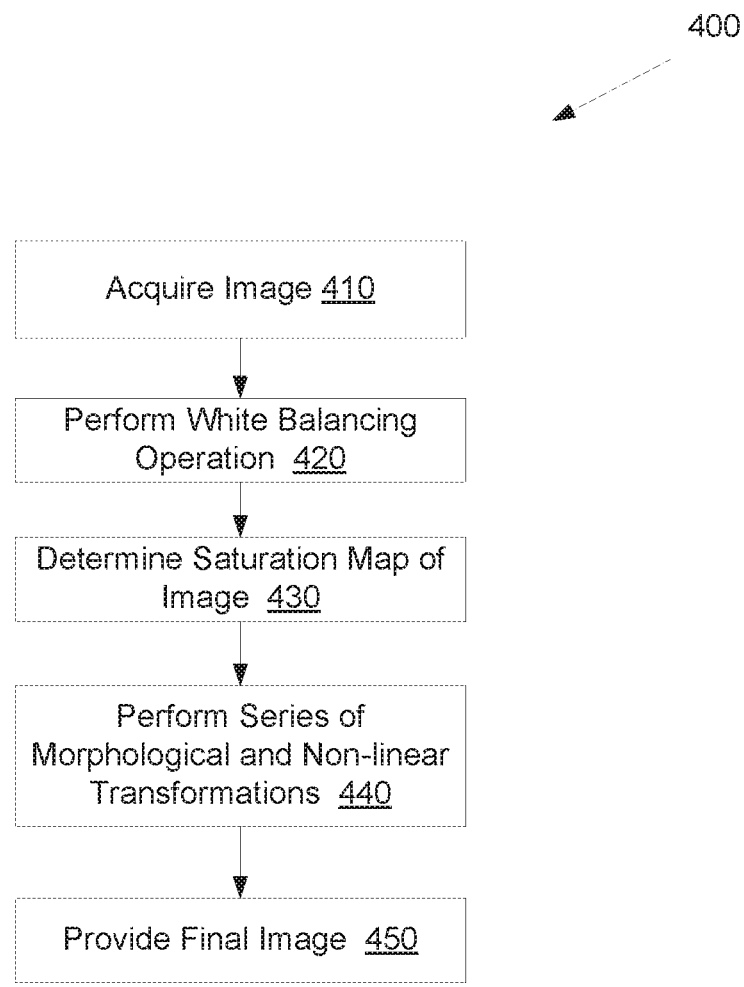
FIG. 4 illustrates a flow diagram of a method for suppressing ambient light in an imaging system, in accordance with embodiments of the present disclosure.

FIG. 4 illustrates a flow diagram of a method 400 for suppressing effects of ambient light in an imaging system. Method 400 is described in relation to the suppression of ambient light entering MLC housing and affecting an optical camera based imaging system used to track MLC leaf positions. However, it should be understood that method 400 may also be used to suppress ambient light in other imaging systems that are subject to ambient light effects and, in particular, where ambient light is constrained in a region and the region is not intended to be illuminated or it is desirable to force the affected region to be dark. The method 400 may be performed by processing logic that comprises hardware (e.g., circuitry, dedicated logic, programmable logic, microcode, etc.), software (e.g., instructions run on a processing device to perform hardware simulation), or a combination thereof.

At block 410, processing logic captures an image of the MLC banks surface and aperture using the feedback system camera 105. At block 420, in one embodiment, optional white balancing operations may be performed if the camera and the internal lighting system do not already result in mechanical surfaces (e.g., leaves of MLC banks) within the collimator housing appearing grayscale (approximately colorless) when viewed from the camera with only internal light present. As the lens of camera 105 discolors and becomes more opaque and the performance of the image sensor of camera 105 changes due to the radiation environment in which the camera operates, a change in color can occur. A white balancing operation may be performed to compensate for such radiation induced changes in the camera system.

In one embodiment, a white balance operation may be performed, for example, if the internal lighting system of the MLC housing 100 is not approximately gray or mapped to gray by some operations. To perform white balancing, a region of interest (ROI) is selected, where the ROI is a mechanical surface of the MLC banks 106, 111 illuminated only by the internal lighting system. For example, an ROI may be designated as the visible surface area of the leaves of MLC bank 106 with a closed aperture (e.g., when the leaves are in a location that prevents ambient light from entering the housing). Following the selection of the ROI, an average RGB pixel value, v, is calculated over all pixels located within the ROI, resulting in an average red pixel value, average green pixel value and an average blue pixel value. For example, in an ROI of two pixels, pixel A has RGB values of [96; 256; 256] and pixel B has RGB values of [32; 0; 128]. The resultant average RGB pixel value is [64; 128; 192]. It should be noted that the pixels' value provided herein are only examples solely intended to aid in explanation of the methods described herein. Although an embodiment using RGB space is discussed herein, in other embodiments, other ways may be used to achieve the effect of minimizing average color saturation for an ROI that may not involve the RGB color space.

Using the average RGB pixel value, a scalar intensity factor, s, is calculated. In one embodiment, the scalar intensity factor includes the average of the three values of the average RGB pixel value. Using the previous example with an average RGB pixel value of [64; 128; 192], the scalar intensity factor would be the average of these three values, resulting in a scalar intensity factor of 128. The values of the average RGB pixel value, v, and the scalar intensity factor, s, may be used to calculate a white balance parameter vector, g. The white balance parameter vector is calculated as the inverse of the average RGB pixel value multiplied by the scalar intensity factor, as shown in the equation below.

$$g=s/v \qquad (1)$$

For example, using the values calculated above, where s=128 and v=[64; 128; 192], the resulting calculation yields a white balance parameter vector of g=128/[64; 128; 192] or [2.0; 1.0; 0.667]. The white balance parameter vector may be applied by pixel-wise multiplication to correct the pixels in subsequent images (as such, the white balance operation 420 may consist only of applying the computed white balance, which may be computed less frequently to account for changes in the system hardware). It should be noted that although there is a single correction g, it is applied to all pixels in subsequent images. For example, given a pixel of RGB values [64; 128; 192], the corrected pixel RGB values would be [64*2.0; 128*1.0; 192*0.667]=[128; 128; 128]. The result is that the corrected pixel has a saturation of zero (i.e., the same values for red, green and blue) and the same average intensity over the three color channels. This gives the appearance of the leaves and other metal surfaces inside the MLC housing 100 as nearly being grayscale (i.e., having a small computed color saturation value). In some embodiments, a different algorithm may be used for the white balancing operation. Examples may be, but are not limited to, normalizing pixel intensities by their L2-norm, perceptual intensity or a metric other than the average RGB value. In one alternative embodiment, the metric may be computed in a different color space, for example, if the camera 105 has a native color space other than RGB. In another embodiment, a camera hardware-based white balance operation may be used when settings are obtained based on an ROI with no ambient light.

At block 430 of method 400, processing logic determines a saturation map for the image captured at block 410. In one embodiment, a saturation map is a representation of the color saturation of each pixel in an image. In another embodiment, the white balancing step may be omitted and the saturation map may be a representation of a distance in color space between each pixel's color and a reference color (i.e. a well-characterized color pertaining to the appearance of the MLC leaf surfaces illuminated by the internal lighting system as captured by the camera in the absence of ambient light).

At block 440 of method 400 a series of morphological and non-linear transformations are applied to the saturation map (or a map of distance in color space to a reference color), S, to produce an attenuation map, A, to suppress ambient light.

In one embodiment, the saturation is modulated by pixel brightness using equation 2, shown below, where V is an intensity (brightness) map.

$$S=S*(1+V) \qquad (2)$$

Using the result of equation 2, a sharp non-linear attenuation curve is created using equation 3, shown below. The desired sharp non-linear attenuation curve may initially have a high slope value with the slope value decreasing rapidly when a specified saturation value is reached. The result is an attenuation curve that highly attenuates pixels with high saturation values due to ambient light, while not attenuating pixels that represent leaf locations.

$$A=1/(a*S^3+b*S^2+c*S+d) \qquad (3)$$

An alternative to the method described in 440 is to compute the attenuation map as 1/(1+S). Alternatively, the first step of 440 (S=S*(1+V)) could be skipped, using the saturation map "directly" as an input to the cubic function.

The cubic coefficients (a, b, c, d) may be determined empirically or computed for a certain type of ambient light (e.g., by fitting a curve to a desired response, where the x axis is saturation and the y axis is the inverse of desired attenuation) to obtain the desired attenuation curve or response for a certain type of ambient light. In this way, the sensitivity of the attenuation can be tuned to ambient light with a certain distribution of saturation value. In another embodiment, any type of suitable transfer function may be used, such as an exponential or higher order polynomial or combination of transcendental functions. A morphological operation (i.e., grayscale opening or erosion of the attenuation map, A) is performed to reduce noise and high frequency artifacts in the corrected image. The use of the morphological operation may be helpful if the source image has a large amount of noise or when the noise of color channels is independent. The ambient light attenuation map is then applied to the original image via pixel-wise multiplication (V=V*A). At block 450, a final image is provided with ambient light being suppressed.

It should be noted that the above described operations are just one method of suppressing effects of ambient light and that, in alternative embodiments, certain ones of the operations of FIG. 4 may be optional or take a simpler form, for example, by use of a linear transformation instead of a non-linear transformation in block 440.

Figure 5:
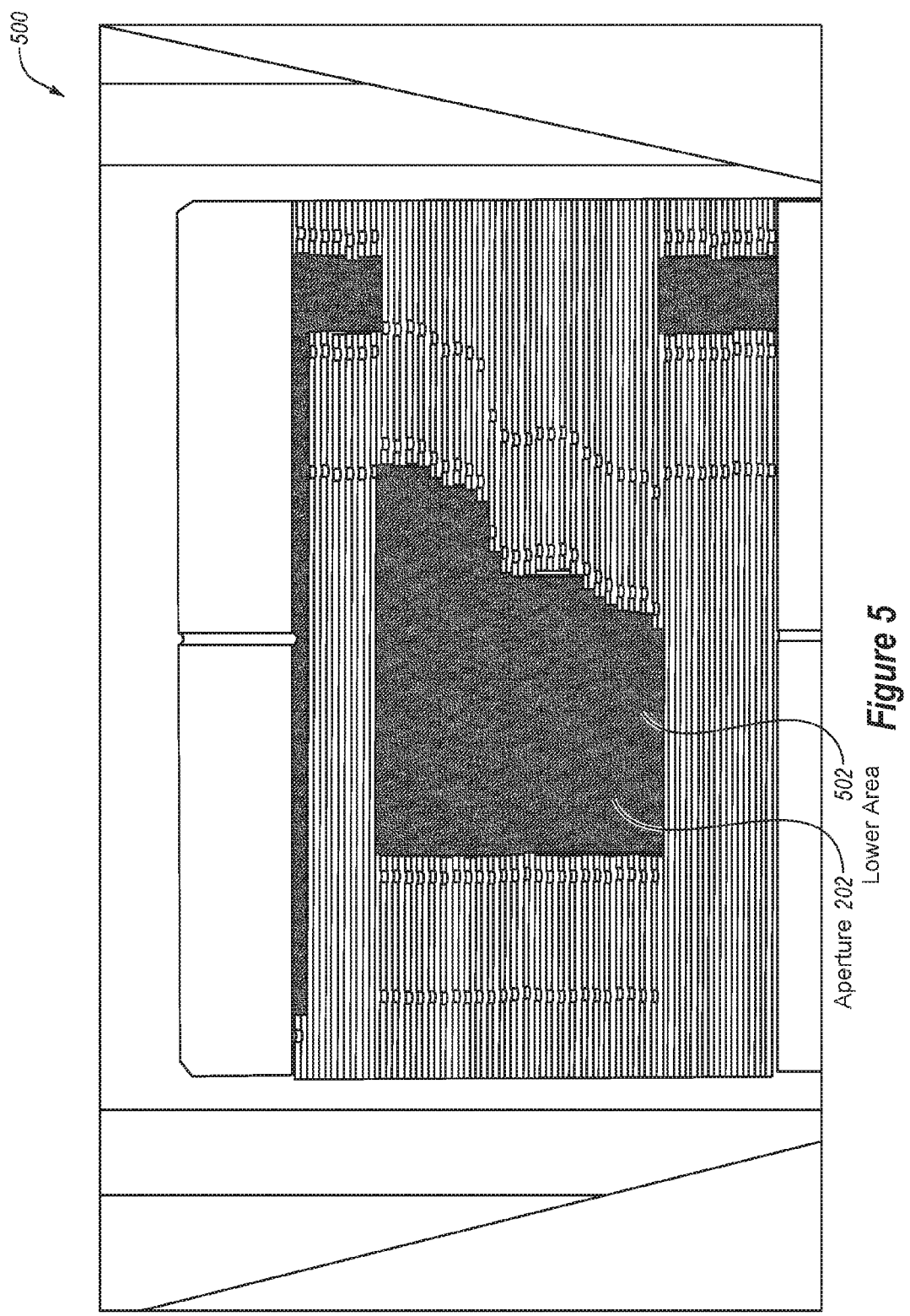
FIG. 5 illustrates the final image created for the feedback camera image shown in FIG. 3, in accordance with embodiments of the present disclosure.

FIG. 5 illustrates the final image 500 created at block 450 for the image 300 shown in FIG. 3 where the darker regions signify higher attenuation values relative to the lighter regions that signify lower attenuation values. The ambient light attenuation map determined at block 440 of FIG. 4 is applied to the entire original image 300 through pixel-wise multiplication (V=V*A). The ambient light attenuation map highly attenuates pixels with high saturation values caused by ambient light, while minimally attenuating pixels that represent leaf locations (that were appropriately white balanced via block 420 or by other technique). The resulting image 500 shows the suppression of ambient light (along with a geometric correction), entering the MLC housing 100 through the aperture 202, for example as more prominently seen in lower area 502 as compared to lower area 302 of FIG. 3. With the ambient light suppressed, the camera-based feedback system can more reliably verify and track the location of the individual leaves of the MLC bank 106.

Figure 6:
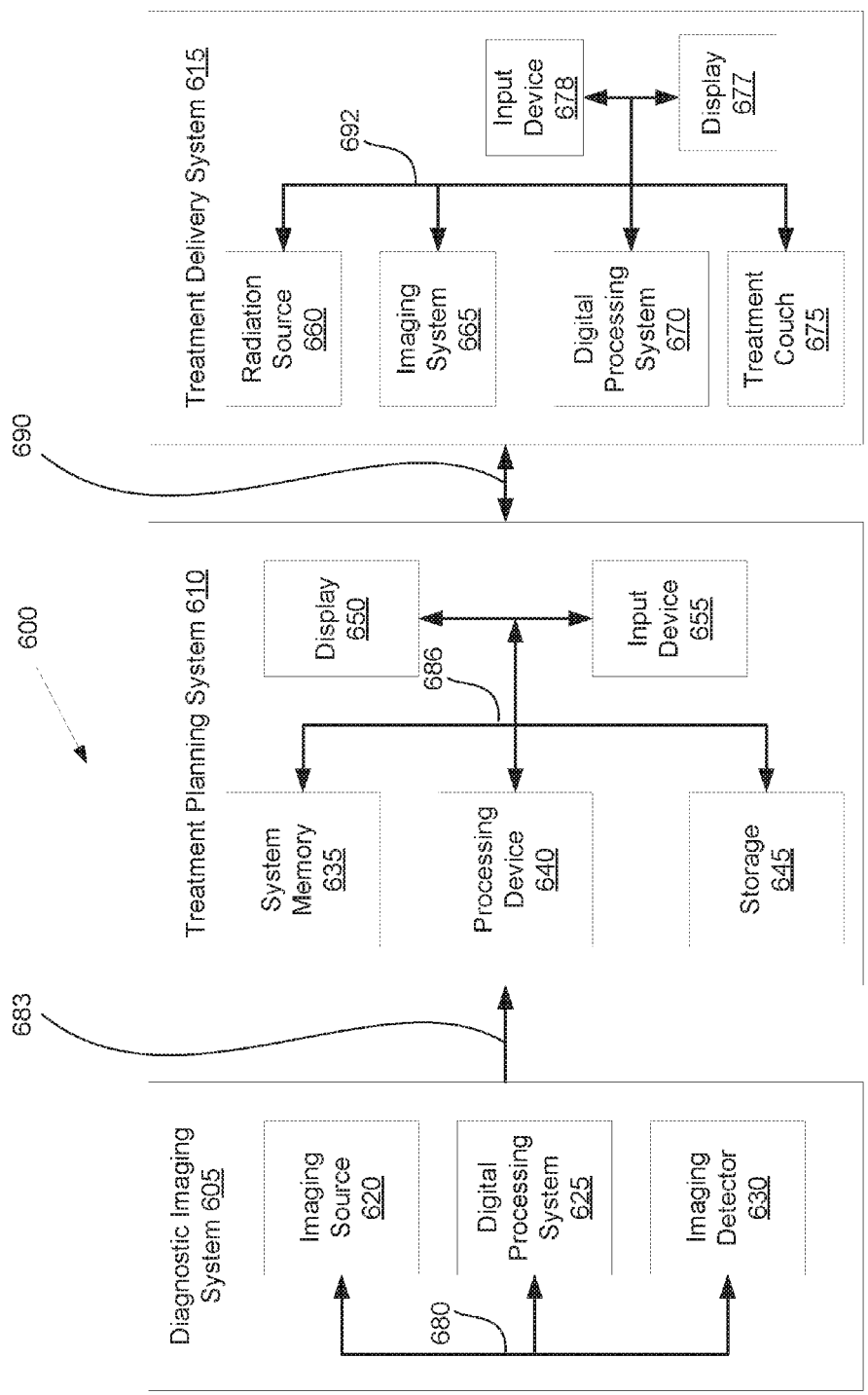
FIG. 6 illustrates one embodiment of systems that may be used in performing radiation treatment, in accordance with embodiments of the present disclosure.

FIG. 6 illustrates one embodiment of systems that may be used in performing radiation treatment. These systems may be used to perform, for example, the methods described above. As described below and illustrated in FIG. 6, a system 600 may include a diagnostic imaging system 605, a treatment planning system 610, a treatment delivery system 615 and a motion detecting system (not shown). In one embodiment, the diagnostic imaging system 605 and the motion detecting system are combined into a single unit.

Diagnostic imaging system 605 may be any system capable of producing medical diagnostic images of a patient that may be used for subsequent medical diagnosis, treatment planning, treatment simulation and/or treatment delivery. For example, diagnostic imaging system 605 may be a computed tomography (CT) system, a magnetic resonance imaging (MRI) system, a positron emission tomography (PET) system, or the like. For ease of discussion, diagnostic imaging system 605 may be discussed below at times in relation to an x-ray imaging modality. In other embodiments, other imaging modalities such as those discussed above may also be used.

In one embodiment, diagnostic imaging system 605 includes an imaging source 620 to generate an imaging beam (e.g., x-rays) and an imaging detector 630 to detect and receive the beam generated by imaging source 620, or a secondary beam or emission stimulated by the beam from the imaging source (e.g., in an MRI or PET scan).

In one embodiment, imaging source 620 and imaging detector 630 may be coupled to a digital processing system 625 to control the imaging operation and process image data. In one embodiment, diagnostic imaging system 605 may receive imaging commands from treatment delivery system 615.

Diagnostic imaging system 605 includes a bus or other means 680 for transferring data and commands among digital processing system 625, imaging source 620 and imaging detector 630. Digital processing system 625 may include one or more general-purpose processors (e.g., a microprocessor), special purpose processor such as a digital signal processor (DSP) or other type of device such as a controller or field programmable gate array (FPGA). Digital processing system 625 may also include other components (not shown) such as memory, storage devices, network adapters and the like. Digital processing system 625 may be configured to generate digital diagnostic images in a standard format, such as the Digital Imaging and Communications in Medicine (DICOM) format, for example. In other embodiments, digital processing system 625 may generate other standard or non-standard digital image formats. Digital processing system 625 may transmit diagnostic image files (e.g., the aforementioned DICOM formatted files) to treatment delivery system 615 over a data link 683, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

In one embodiment, treatment delivery system 615 includes a therapeutic and/or surgical radiation source 660 to administer a prescribed radiation dose to a target volume in conformance with a treatment plan. Treatment delivery system 615 may also include imaging system 665 to perform computed tomography (CT) such as cone beam CT, and images generated by imaging system 665 may be two-dimensional (2D) or three-dimensional (3D).

Treatment delivery system 615 may also include a digital processing system 670 to control radiation source 660, receive and process data from diagnostic imaging system 605 and/or treatment planning system 610, and control a patient support device such as a treatment couch 675. Digital processing system 670 may be connected to or a part of the camera feedback system described above and operate on the images captured by camera 105 of FIG. 1. Digital processing system 670 may be configured to register 2D radiographic images received from diagnostic imaging system 605, from two or more stereoscopic projections, with digitally reconstructed radiographs (DRRs) generated by digital processing system 625 in diagnostic imaging system 605 and/or DRRs generated by processing device 640 in treatment planning system 610. Digital processing system 670 may include a processing device that represents one or more general-purpose processors (e.g., a microprocessor), special purpose processor such as a digital signal processor (DSP) or other type of device such as a controller or field programmable gate array (FPGA). The processing device of digital processing system 670 may be configured to execute instructions to perform treatment delivery operations, for example, the method 400 described above in regards to FIG. 4.

In one embodiment, digital processing system 670 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 670 may also include a storage device, representing one or more storage devices (e.g., a magnetic disk drive or optical disk drive) for storing information and instructions. The storage device may be used for storing instructions for performing the treatment delivery steps discussed herein. Digital processing system 670 may be coupled to radiation source 660 and treatment couch 675 by a bus 692 or other type of control and communication interface.

Digital processing system 670 may implement methods to manage timing of diagnostic x-ray imaging in order to maintain alignment of a target with a radiation treatment beam delivered by the radiation source 660.

In one embodiment, the treatment delivery system 615 includes an input device 678 and a display 677 connected with digital processing system 670 via bus 692. The display 677 can show trend data that identifies a rate of target movement (e.g., a rate of movement of a target volume that is under treatment). The display can also show a current radiation exposure of a patient and a projected radiation exposure for the patient. The input device 678 can enable a clinician to adjust parameters of a treatment delivery plan during treatment.

Treatment planning system 610 includes a processing device 640 to generate and modify treatment plans and/or simulation plans. Processing device 640 may represent one or more general-purpose processors (e.g., a microprocessor), special purpose processor such as a digital signal processor (DSP) or other type of device such as a controller or field programmable gate array (FPGA). Processing device 640 may be configured to execute instructions for performing simulation generating operations and/or treatment planning operations discussed herein.

Treatment planning system 610 may also include system memory 635 that may include a random access memory (RAM), or other dynamic storage devices, coupled to processing device 640 by bus 686, for storing information and instructions to be executed by processing device 640. System memory 635 also may be used for storing temporary variables or other intermediate information during execution of instructions by processing device 640. System memory 635 may also include a read only memory (ROM) and/or other static storage device coupled to bus 686 for storing static information and instructions for processing device 640.

Treatment planning system 610 may also include storage device 645, representing one or more storage devices (e.g., a magnetic disk drive or optical disk drive) coupled to bus 686 for storing information and instructions. Storage device 645 may be used for storing instructions for performing the treatment planning steps discussed herein.

Processing device 640 may also be coupled to a display device 650, such as a cathode ray tube (CRT) or liquid crystal display (LCD), for displaying information (e.g., a 2D or 3D representation of the VOI) to the user. An input device 655, such as a keyboard, may be coupled to processing device 640 for communicating information and/or command selections to processing device 640. One or more other user input devices (e.g., a mouse, a trackball or cursor direction keys) may also be used to communicate directional information, to select commands for processing device 640 and to control cursor movements on display 650.

Treatment planning system 610 may share its database (e.g., data stored in storage 645) with a treatment delivery system, such as treatment delivery system 615, so that it may not be necessary to export from the treatment planning system prior to treatment delivery. Treatment planning system 610 may be linked to treatment delivery system 615 via a data link 690, which in one embodiment may be a direct link, a LAN link or a WAN link.

It should be noted that when data links 683, 686, and 690 are implemented as LAN or WAN connections, any of diagnostic imaging system 605, treatment planning system 610 and/or treatment delivery system 615 may be in decentralized locations such that the systems may be physically remote from each other. Alternatively, any of diagnostic imaging system 605, treatment planning system 610, and/or treatment delivery system 615 may be integrated with each other in one or more systems.

Figure 7:
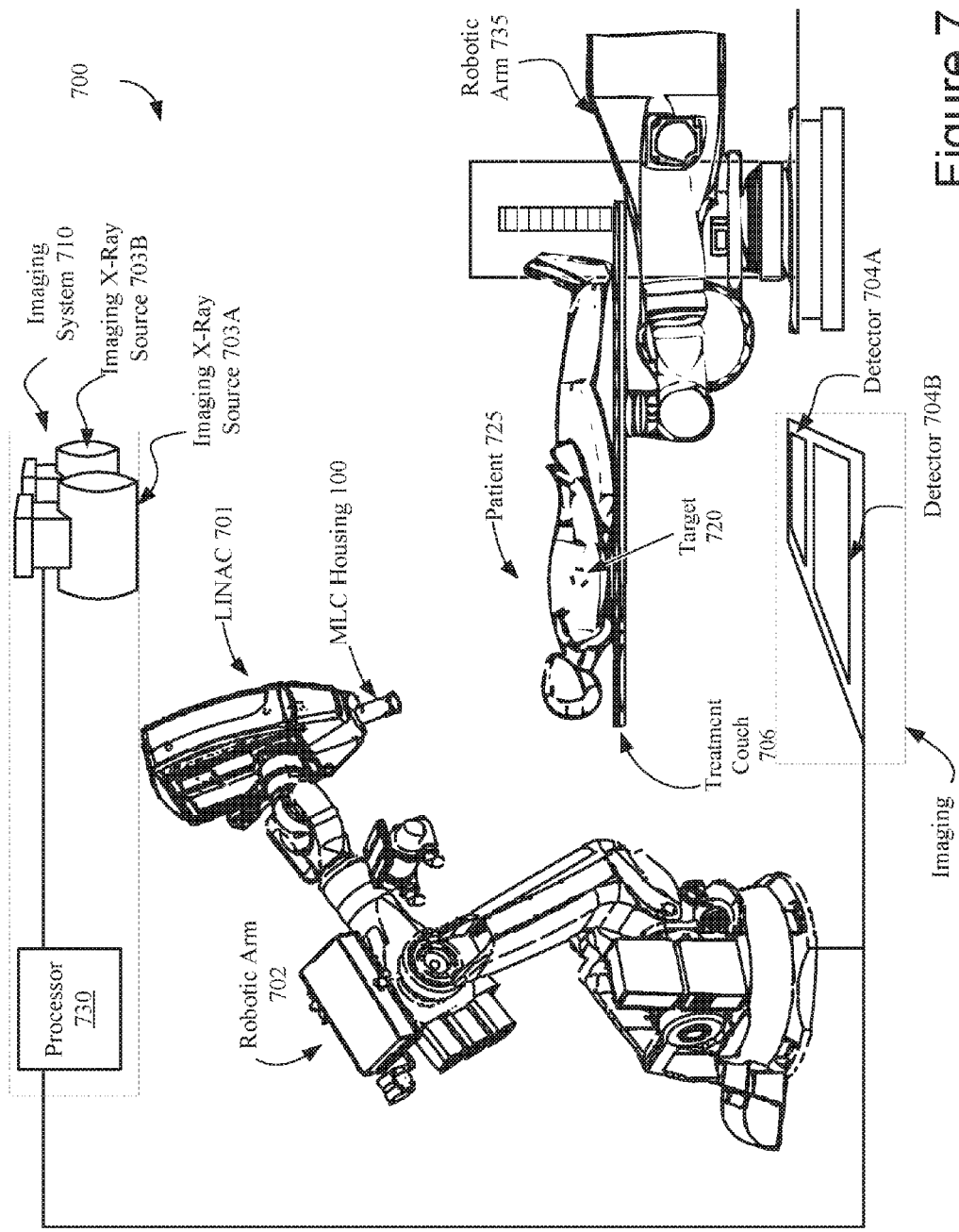
FIG. 7 illustrates an image-guided radiation treatment system, in accordance with embodiments of the present disclosure.
Figure 8:
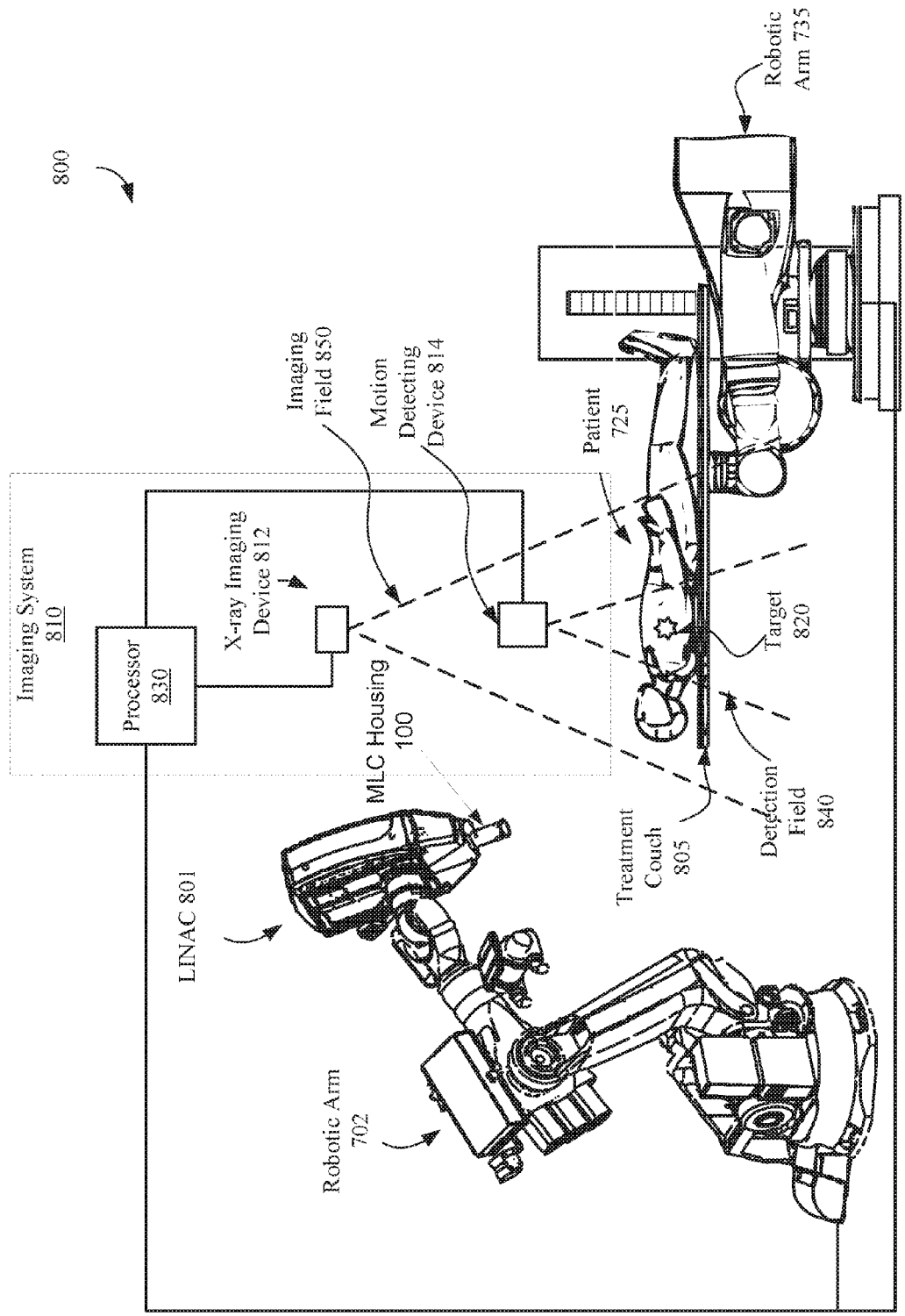
FIG. 8 illustrates a gantry based image-guided radiation treatment system, in accordance with embodiments of the present disclosure.

FIGS. 7 and 8 illustrate configurations of image-guided radiation treatment systems 700 and 800, in accordance with embodiments of the present disclosure. In the illustrated embodiments, the radiation treatment systems 700 and 800 include a linear accelerator (LINAC) 701 that acts as a radiation treatment source, and an MLC housing 100. In one embodiment, the LINAC 701 and MLC housing 100 are mounted on the end of a robotic arm 702 having multiple (e.g., 5 or more) degrees of freedom in order to position the LINAC 701 and MLC housing 100 to irradiate a pathological anatomy (e.g., target 720) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 701 and MLC housing 100 may be mounted on a gantry based system to provide isocentric beam paths. In one particular embodiment, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry.

In one embodiment, the LINAC 701 and MLC housing 100 may be positioned at multiple different nodes (pre-defined positions at which the robot stops and radiation may be delivered) during treatment by moving the robotic arm 735. At the nodes, the LINAC 701 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 700 to 3200, or more preferably 50 to 300.

Referring to FIG. 7, radiation treatment system 700, in accordance with one embodiment of the present disclosure, includes an imaging system 665 having a processor 730 connected with x-ray sources 703A and 703B and fixed x-ray detectors 704A and 704B. Alternatively, the x-ray sources 703A, 703B and/or x-ray detectors 704A, 704B may be mobile, in which case they may be repositioned to maintain alignment with the target 720, or alternatively to image the target from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 701 serves as an imaging source (whether gantry or robot mounted), where the LINAC power level is reduced to acceptable levels for imaging.

Imaging system 665 may perform computed tomography (CT) such as cone beam CT, and images generated by imaging system 665 may be two-dimensional (2D) or three-dimensional (3D). The two x-ray sources 703A and 703B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 706 during treatment) and to illuminate imaging planes of respective detectors 704A and 704B after passing through the patient. In one embodiment, imaging system 665 provides stereoscopic imaging of the target 720 and the surrounding volume of interest (VOI). In other embodiments, imaging system 665 may include more or less than two x-ray sources and more or less than two detectors, and any of the detectors may be movable rather than fixed. In yet other embodiments, the positions of the x-ray sources and the detectors may be interchanged. Detectors 704A and 704B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Referring to FIG. 8, in alternative embodiments an imaging system 810 includes a motion detection device 812 to determine target motion, the motion detecting device 814 having a detection field 840. The motion detecting device 814 may detect external patient motion (such as chest movement during respiration) that occurs within an 850. The motion detecting device 814 can be any sensor or other device capable of identifying target movement. The motion detecting device 814, may be, for example an optical sensor such as a camera, a pressure sensor, an electromagnetic sensor, or some other sensor that can provide motion detection without delivering ionizing radiation to a user (e.g., a sensor other than an x-ray imaging system). In one embodiment, the motion detecting device 814 acquires measurement data indicative of target motion in real-time. Alternatively, the measurement data may be acquired at a frequency that is higher (potentially substantially higher) than can be achieved or than is desirable with x-ray imaging (due to ionizing radiation delivered to the patient with each x-ray image). In one embodiment, the motion detecting device 814 does not provide a high absolute position accuracy. Instead, the motion detecting device 814 may provide sufficient relative position accuracy to detect patient movement and/or target movement.

In one embodiment, the motion detecting device 814 is an optical system, such as a camera. The optical system may track the position of light-emitting diodes (LEDs) situated on patient 725. Alternatively, the optical system may directly track a surface region of patient 725, as distinguished from tracking LEDs on the patient. There may be a correlation between movement of the target and movement of the LEDs and/or surface region of the patient 725. Based on the correlation, when motion of the LEDs and/or surface region is detected, it can be determined that the target 720 has also moved sufficiently to require another diagnostic x-ray image to precisely determine the location of the target.

Figure 9:
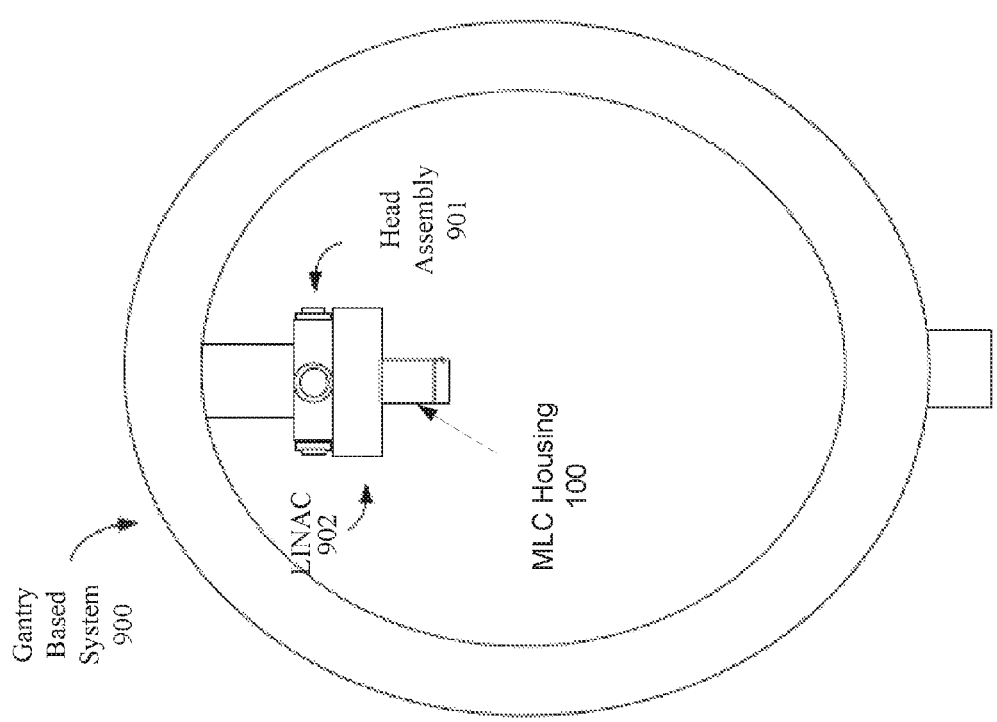
FIG. 9 illustrates a gantry based intensity modulated radiotherapy (IMRT) system in accordance with embodiments of the present disclosure.

FIG. 9 illustrates one embodiment of a gantry based (isocentric) intensity modulated radiotherapy (IMRT) system 900. In a gantry based system 900, a radiation source (e.g., a LINAC) 902 having a head assembly 901 and MLC housing 100 are mounted on the gantry in such a way that they rotate in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. The resulting system generates arbitrarily shaped radiation beams that intersect each other at the isocenter to deliver a dose distribution to the target. In one embodiment, the gantry based system 900 may be a c-arm based system.

It will be apparent from the foregoing description that aspects of the present disclosure may be embodied, at least in part, in software. That is, the techniques may be carried out in a computer system or other data processing system in response to its processor, such as digital processing system 670, for example, executing sequences of instructions contained in a memory. In various embodiments, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as digital processing system 670.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "processing," "computing," "generating," "comparing" "determining," "calculating," "performing," "identifying," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present disclosure are not described with reference to any particular programming language. It will be appreciated that a variety of programming languages may be used to implement embodiments of the present disclosure.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary embodiments thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method comprising:
    illuminating, with a lighting system disposed inside a housing of a multi-leaf collimator (MLC), leaves of the MLC with a first light;
    receiving ambient light inside the housing of the MLC through an aperture of the MLC;

capturing, using an imaging system having optics situated inside the housing of the MLC, a first image of the leaves of the MLC illuminated with the first light and the ambient light;

suppressing, by a processing device, the ambient light in the first image to generate a second image of the leaves of the MLC; and detecting a feature of the leaves of the MLC in the second image.

2. The method of claim 1, wherein suppressing ambient light in the first image comprises suppressing ambient light near leading edges of the leaves that shape the aperture of the MCL.

3. The method of claim 1, further comprising tracking a position of a leaf of the MLC using the detected feature in the second image.

4. The method of claim 1, wherein suppressing the ambient light to generate the second image comprises:
generating an attenuation map for the first image; and
generating the second image using the attenuation map.

5. The method of claim 4, wherein suppressing the ambient light to generate the second image further comprises determining a saturation map for the first image prior to generating the attenuation map, and wherein generating the attenuation map comprises applying a series of morphological and non-linear transformations to the saturation map.

6. The method of claim 4, wherein generating the second image comprises applying the attenuation map to the first image via pixel-wise multiplication.

7. The method of claim 1, wherein suppressing the ambient light comprises:
receiving a first image, wherein the first image comprises a first plurality of pixels having a corresponding first plurality of pixel values;
generating a second plurality of pixel values by performing a multiplication operation each pixel value of the first plurality of pixel values; and
generating a third plurality of pixel values using a polynomial function having coefficients determined to achieve a certain response to saturation levels, wherein the third plurality of pixel values comprises the second image.

8. The method of claim 4, wherein the saturation map comprises a distance in color space, in the first image, between a pixel's color and a reference color.

9. The method of claim 4, wherein the saturation map is a representation of a color saturation of each pixel in the first image and wherein the method further comprises:
performing a white balancing operation on the first image.

10. The method of claim 9, wherein performing the white balancing operation comprises:
determining a region of interest associated with the first image;
calculating an average Red Green Blue (RGB) pixel value for each of plurality of pixels associated with the region of interest in the first image;
calculating an intensity factor based on the average RGB pixel values; and
calculating a white balance parameter vector based on the average RGB pixel values and the intensity factor.
applying the white balance parameter vector to a subsequent plurality of pixels, in a subsequent image, corresponding to similar positions of the plurality of pixels in the first image.

11. The method of claim 10, wherein the white balance parameter vector is applied by pixel-wise multiplication to correct the plurality of pixels in subsequent images.

12. The method of claim 4, wherein generating the attenuation map comprises:
creating an attenuation curve for pixels in the first image, wherein the attenuation curve attenuates pixels with a high saturation value due to ambient light and wherein the attenuation curve does not attenuate pixels that represent a collimator leaf location in the image.

13. The method of claim 12, further comprising:
performing a morphological operation on the attenuation map to reduce noise and high frequency artifacts in the attenuation map.

14. The method of claim 1, wherein the lighting system is an LED lighting system.

15. The method of claim 1, wherein the first light is white light.

16. The method of claim 1, wherein the first light has a first primary wavelength and the ambient light has a second primary wavelength, and wherein the first primary wavelength is selected to be dissimilar to the second primary wavelength.

17. A radiation treatment system comprising:
a multi-leaf collimator (MLC) disposed within a housing;
a lighting system, disposed within the housing of the MLC, to illuminate leaves of the MLC with a first light;
an imaging system, having optics situated inside the housing of the MLC to capture a first image of the leaves of the MLC illuminated with the first light and an ambient light;
a memory to store a plurality of images of leaves of the MLC; and
a processing device, operatively coupled to the memory, the processing device to:
suppress the ambient light in the first image to generate a second image of the leaves of the MLC; and
detect a feature of the leaves of the MLC in the second image.

18. The radiation treatment system of claim 17, wherein to suppress the ambient light in the first image the processing device is further to suppress ambient light near leading edges of the leaves that shape an aperture of the MLC.

19. The radiation treatment system of claim 17, wherein the processing device is further to track a position of a leaf of the MLC using the detected feature with the second image.

20. The radiation treatment system of claim 19, wherein the first image comprises a first plurality of pixels having a corresponding first plurality of pixel values and wherein to suppress the ambient light the processing device is further to:
generate a second plurality of pixel values by performing a multiplication operation on each pixel value of the first plurality of pixel values; and
generate a third plurality of pixel values using a polynomial function having coefficient determined to obtain a response for a certain type of the ambient light, wherein the third plurality of pixels comprise the second image.

21. The radiation treatment system of claim 17, wherein the imaging system comprises optics situated inside the housing of the MLC.

22. The radiation treatment system of claim 17, wherein to suppress the ambient light the processing device is further to:
generate an attenuation map for the first image; and
generate the second image using the attenuation map.

23. A non-transitory machine-readable storage medium including instructions that, when accessed by a processing device, cause the processing device to:

receive a first image of leaves of a multi-leaf collimator (MLC) illuminated with a first light and an ambient light;

suppress, by the processing device, the ambient light in the first image to generate a second image of the leaves of the MLC; and detect, by the processing device, a feature of the leaves of the MLC in the second image.

24. The non-transitory machine-readable storage medium of claim 23, wherein to suppress the ambient light to generate the second image the processing device is further to:

generate an attenuation map for the first image; and
generate the second image using the attenuation map.

* * * * *